US00PP12141P2

(12) United States Plant Patent
Rother

(10) Patent No.: US PP12,141 P2
(45) Date of Patent: Oct. 16, 2001

(54) PETUNIA PLANT NAMED 'VELVET BLUE WREN'

(76) Inventor: Reinhard W. Rother, P.B. 327, Emerald, Victoria (AU)

( * ) Notice: Subject to any disclaimer, the term of this patent is extended or adjusted under 35 U.S.C. 154(b) by 0 days.

(21) Appl. No.: 09/545,907

(22) Filed: Apr. 9, 2000

(51) Int. Cl.[7] ..... A01H 5/00
(52) U.S. Cl. ..... Plt./356

(58) Field of Search ..... Plt./356

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Petunia plant named 'Velvet Blue Wren', characterized by its initially upright then outwardly spreading and trailing plant habit; freely and continuous branching growth habit; dark green leaves; relatively early flowering; and dark-violet-colored flowers that are velvety in texture.

1 Drawing Sheet

BACKGROUND OF THE INVENTION

The present Invention relates to a new and distinct cultivar of Petunia plant, botanically known as *Petunia×hybrida*, and hereinafter referred to by the cultivar name Velvet Blue Wren.

The new Petunia is a product of a planned breeding program conducted by the Inventor in Emerald, Victoria, Australia. The new Petunia originated from a cross made by the Inventor of a proprietary selection of *Petunia×hybrida* identified as code number 4290 as the female, or seed, parent with a proprietary selection of *Petunia×hybrida* identified as code number 892 as the male, or pollen, parent. The new Petunia was selected in October, 1993 on the basis of its unique flower color and velvet-like petal texture.

Plants of the new Petunia are more outwardly spreading and differ in flower color compared to plants of the female parent selection. Compared to plants of the male parent selection, plants of the new Petunia have smaller flowers, smaller leaves and also differ in flower color.

Asexual reproduction of the new cultivar by terminal cuttings taken at Emerald, Victoria, Australia, has shown that the unique features of this new Petunia are stable and reproduced true to type in successive generations.

SUMMARY OF THE INVENTION

Plants of the cultivar Velvet Blue Wren have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Velvet Blue Wren'. These characteristics in combination distinguish 'Velvet Blue Wren' as a new and distinct cultivar:

1. Initially upright then outwardly spreading and trailing plant habit; compact.
2. Freely and continuous branching.
3. Dark green leaves.
4. Relatively early flowering.
5. Dark violet-colored flowers that are velvety in texture.

Plants of the cultivar Velvet Blue Wren can be compared to plants of the cultivar Revolution Violet, disclosed in U.S. Plant Pat. No. 9,342. However in side-by-side comparisons conducted by the Inventor in Emerald, Victoria, Australia, plants of the cultivar Velvet Blue Wren have darker violet-colored flowers and flower earlier than plants of the cultivar Revolution Violet.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Petunia.

The photograph at the top of the sheet comprises a top perspective view of typical flowering plants of 'Velvet Blue Wren'.

The photograph at the bottom of the sheet is a close-up view of a typical opened flower from the top and side perspectives, upper and lower surfaces of typical leaves, and a typical opening flower bud of 'Velvet Blue Wren'.

DETAILED BOTANICAL DESCRIPTION

In the following description, color references are made to The Royal Horticultural Society Colour Chart except where general terms of ordinary dictionary significance are used. Plants grown in 25-cm containers were used for the following description with three plants per container. Plants were grown under full sun field conditions which closely approximate commercial production conditions during the spring in Bonsall, Calif. Day temperatures ranged from 13 to 35° C. and night temperatures ranged from 7 to 18° C.

Botanical classification: *Petunia×hybrida* cultivar Velvet Blue Wren.

Parentage:

*Female parent.*—Proprietary selection of *Petunia×hybrida* identified as code number 4290, not patented.

*Male parent.*—Proprietary selection of *Petunia×hybrida* identified as code number 892, not patented.

Propagation:

*Type cutting.*—Terminal vegetative cuttings.

*Time to initiate roots, summer.*—About 12 to 18 days at 22° C.

*Time to initiate roots, winter.*—About 15 to 21 days at 22° C.

*Rooting habit.*—Numerous, fine, fibrous, and well-branched.

Plant description:

*Form.*—Indeterminate; compact; initially upright, then outwardly spreading and trailing; viscid and glandular pubescent.

*Usage.*—Appropriate for hanging baskets and patio containers.

*Crop time.*—About 8 weeks are required to produce finished flowering plants in 10-cm containers.

*Plant height* (*from soil level to top of plant plane*).—About 15.5 cm.

*Area of spread.*—About 23 cm.

*Vigor.*—Moderate to vigorous.

*Branching habit.*—Freely branching with about seven or eight lateral branches per plant; removal of terminal apices (pinching) enhances branching.

*Lateral branches.*— Length: About 17 cm. Diameter: About 3 mm. Internode length: About 2.8 cm. Texture: Pubescent; viscid, glandular. Color: 144A to 144B.

*Foliage description.*—Leaves simple, generally symmetrical and long persisting. Leaf arrangement alternate before flowering, opposite after flowering. Quantity per lateral branch: Typically about 12. Length: About 3.75 cm. Width: About 2.25 cm. Aspect: Typically horizontal. Shape: Elliptic. Apex: Broadly acute to rounded. Base: Attenuate. Margin: Entire. Texture: Sparse pubescence on both surfaces; glandular, viscid. Color: Young foliage, upper surface: 137C. Young foliage, lower surface: 137D. Mature foliage, upper surface: 137A; venation, 137D. Mature foliage, lower surface: 137D; venation, 137D. Petiole: Length: About 5 mm. Diameter: About 3 mm. Color: 144B.

Flower description:

*Flower type and habit.*—Medium-sized flowers; flowers face mostly upward; single, axillary. Flowers persistent. Flowering continuous.

*Natural flowering season.*—Long day responsive; flowering from spring through fall. Plants starting flowering about four to six weeks after rooting.

*Quantity.*—Freely flowering with about 20 flowers and flower buds per plant.

*Fragrance.*—None detected.

*Flower longevity on the plant.*—Good, about 3 to 5 days.

*Flower buds* (*just showing color*).— Length: About 2.8 cm. Diameter: About 8 mm. Shape: Elongate, roughly ovate with slightly ruffled apex. Color: 79D to 79C.

*Corolla.*— Arrangement/appearance: Single whorl of five petals, fused into flared trumpet, slightly ruffled. Flower diameter: About 5 by 5.3 cm. Flower tube length: About 3 cm. Flower throat diameter, distal end: About 1 cm. Flower tube diameter, proximal end; About 3 mm. Petal length from throat: Upper three petal lobes, about 2.2 cm; lower two petal lobes, about 2.5 cm. Petal width: About 2.5 cm. Petal shape: Rounded, spatulate. Petal apex; Rounded and very slightly sinuate. Petal margin: Entire. Texture: Smooth and very velvet-like. Color: Petal, upper surface, when opening: 79A. Petal, lower surface, when opening: 79D to 79C; central creases, 79A. Petal, upper surface, opened flower: Slightly brighter than 79B to 83A; veins, 79B to 83A. Petal, lower surface, opened flower: 79C; veins, 79B; central creases, 79A. Flower throat (inside); Ground, 83D; veins, 83A. Flower tube (outside): Ground, 83B to 83C; veins, 83A; base, 144D.

*Sepals.*—Quantity: Five. Shape: Strap-like or narrowly elliptic. Apex: Rounded. Margin: Entire. Texture: Smooth; glandular, viscid. Color: Upper surface: 137B. Lower surface: 137D.

*Peduncle.*— Strength: Moderately strong. Angle: Upright to about 45°, dependent on lateral stem orientation. Length: About 4 cm. Color: 144B.

*Reproductive organs.*— Stamens: Stamen number per flower/arrangement: About five; adnate to corolla tube base. Anther shape: Ovoid. Anther length: About 2 mm. Anther color: 156A. Pollen amount: Scarce. Pollen color: 156B. Pistils: Pistil quantity per flower: One. Pistil length: About 2.3 cm. Stigma shape: Flattened; slightly bi-lobate. Stigma color: 138A. Style length: About 2 cm. Style color: 144B. Ovary color: 144D.

*Seed.*—Seed production has not been observed.

Disease resistance: Plants of the new Petunia have not been noted to be resistant to pathogens common to Petunia.

It is claimed:

1. A new and distinct cultivar of Petunia plant named 'Velvet Blue Wren', as illustrated and described.

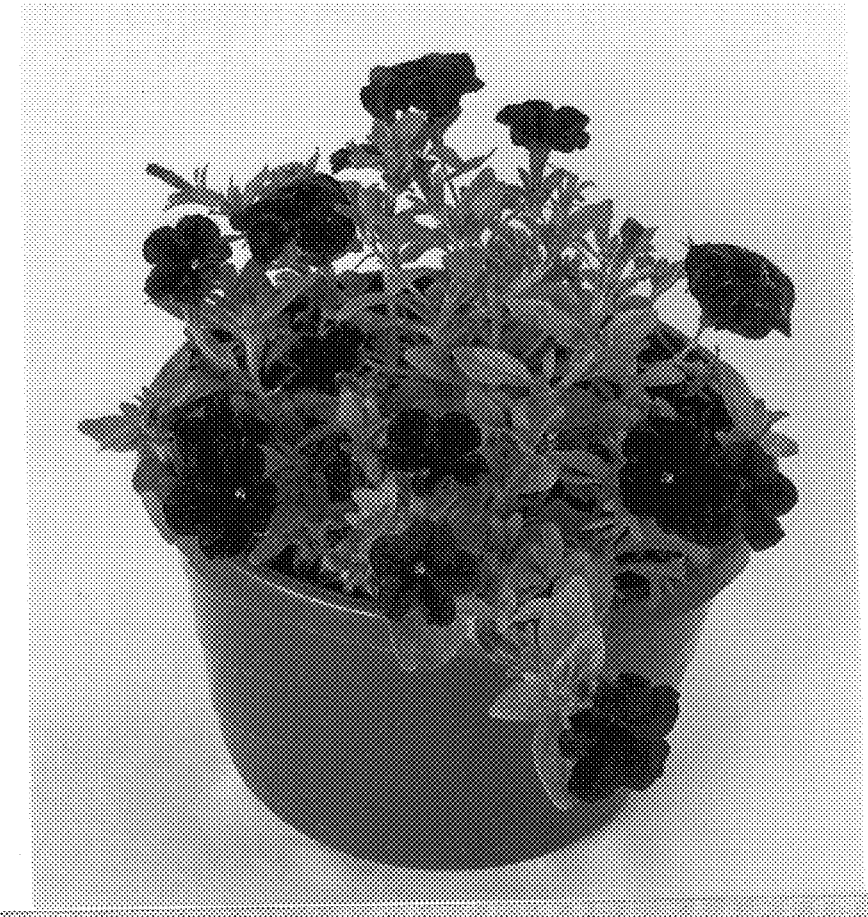
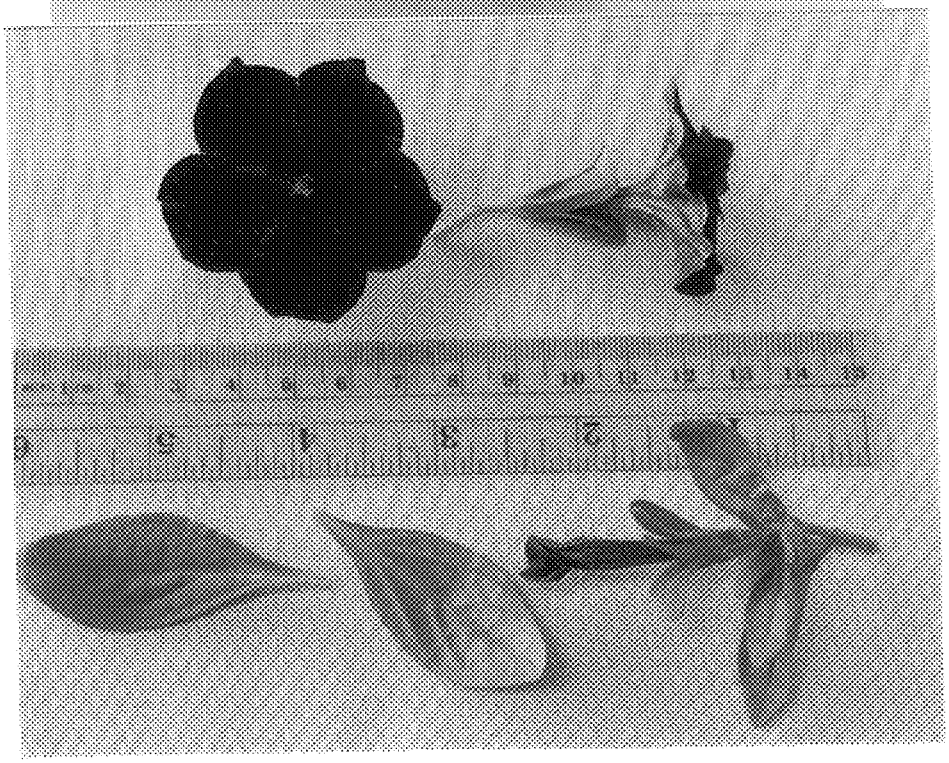

* * * * *